(12) United States Patent
Kiani

(10) Patent No.: US 11,298,468 B2
(45) Date of Patent: Apr. 12, 2022

(54) INJECTION ANALGESIA SYSTEM

(71) Applicant: Nessa Kiani, Laguna Niguel, CA (US)

(72) Inventor: Nessa Kiani, Laguna Niguel, CA (US)

(*) Notice: Subject to any disclaimer, the term of this patent is extended or adjusted under 35 U.S.C. 154(b) by 525 days.

(21) Appl. No.: 16/228,048

(22) Filed: Dec. 20, 2018

(65) Prior Publication Data

US 2019/0192788 A1 Jun. 27, 2019

Related U.S. Application Data

(63) Continuation of application No. 14/735,124, filed on Jun. 9, 2015, now Pat. No. 10,195,366.

(60) Provisional application No. 62/009,901, filed on Jun. 9, 2014.

(51) Int. Cl.
*A61M 5/42* (2006.01)

(52) U.S. Cl.
CPC ............ *A61M 5/422* (2013.01); *A61M 5/427* (2013.01)

(58) Field of Classification Search
CPC ........ A61M 5/427; A61M 5/422; A61M 5/42; A61M 25/0074; A61M 5/3287; A61M 2025/0057
See application file for complete search history.

(56) References Cited

U.S. PATENT DOCUMENTS

| | | | |
|---|---|---|---|
| 1,934,046 A | | 11/1933 | Mario |
| 4,943,284 A | * | 7/1990 | Erlich ................. A61M 25/002 206/365 |
| 10,195,366 B1 | | 2/2019 | Kiani |
| 2003/0078546 A1 | * | 4/2003 | Jensen ................ A61M 5/3202 604/232 |
| 2004/0147901 A1 | | 7/2004 | Py et al. |
| 2004/0199112 A1 | * | 10/2004 | Dalton .................. A61M 5/326 604/110 |
| 2009/0234306 A1 | | 9/2009 | Vitaris |
| 2011/0166498 A1 | | 7/2011 | Shantha |

* cited by examiner

*Primary Examiner* — Lauren P Farrar
*Assistant Examiner* — Hamza A Darb
(74) *Attorney, Agent, or Firm* — Knobbe, Martens, Olson & Bear, LLP

(57) ABSTRACT

An injection analgesia system advantageously numbs a patient's skin around an injection site. An injection window guides a caregiver's injection placement to a relatively small area while allowing standard injection procedures to be followed, such as stretching the skin and puncturing the site with a jabbing motion. The injection analgesia system has a needle shield and an analgesia, which are layered together and applied to a skin surface. A needle shield window and a analgesia window align to form the injection window. Advantageously, the needle shield may fold and/or wrap around the injection needle for sharp object protection during and after needle disposal.

12 Claims, 6 Drawing Sheets

VIEW A-A

VIEW A-A

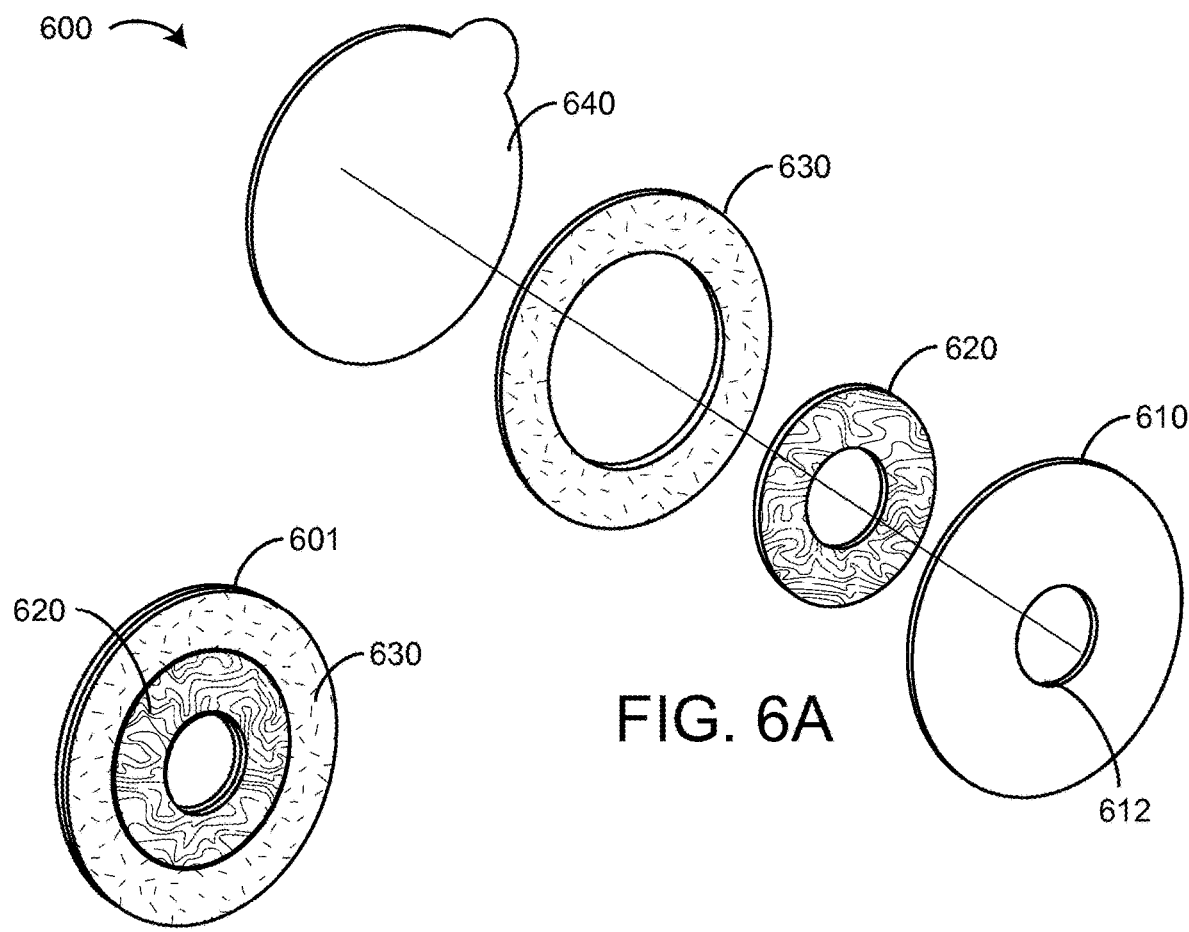
FIG. 6A
FIG. 6B
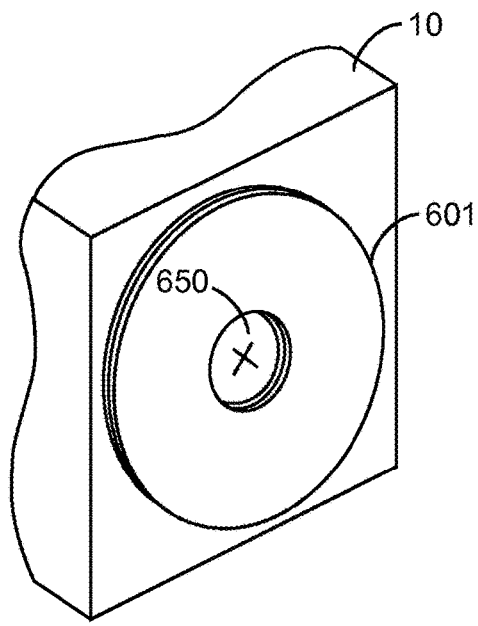
FIG. 6C

INJECTION ANALGESIA SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

SUMMARY OF THE INVENTION

One aspect of an injection analgesia system is to take pain away from flu shots and vaccines. A substantial portion of Americans are not vaccinated for prevalent and reoccurring communicable diseases, such as the flu. A major cause of this neglect is the pain associated with injection.

In an embodiment, an injection analgesia system has a flexible suction cup with an open front end and closed back end. A grip extends from the back end. A needle guide is disposed through the grip and into the suction cup. The needle guide is configured to guide an injection needle to an injection site. An analgesia is disposed within the suction cup. The analgesia is dispersed along a skin surface when the suction cup is attached to the skin surface, so as to reduce pain due to an injection.

In an embodiment, an injection analgesia system has a sealed adhesive patch with a needle shield layer defining a needle opening, an analgesia layer disposed proximate the opening, an adhesive layer disposed distal the opening and a removable backing disposed over the analgesia layer and adhesive layer. The backing is removed so as to unseal the adhesive layer and expose the analgesia layer to a skin surface.

In an embodiment, an injection analgesia system has a substrate with a first side and a second side. An opening is defined by the substrate. An analgesia is disposed on the second side proximate the opening, and an attachment mechanism is disposed proximate at least one of the substrate first side and the second side so as to secure the substrate second side to a skin surface and allow the analgesia to numb the skin surface proximate the opening. In various embodiments, the attachment mechanism is disposed proximate the second side. A second substrate is disposed proximate the first side and extends beyond the edges of the first substrate. An attachment mechanism is disposed proximate the outer edges of the second substrate so as to secure both the first substrate and the second substrate to the skin surface. The attachment mechanism may be disposed around the outer edges of the analgesia distal the opening. A backing layer is disposed over the analgesia and the adhesive distal the substrate. The backing layer protects the attachment mechanism from contamination and is removable prior to attachment of the substrate to the skin surface so as to expose the attachment mechanism and the analgesia to the skin surface. In various embodiments, the attachment mechanism is an adhesive or a suction cup.

In a further embodiment, an injection analgesia method provides a needle shield having a skin side and a needle side. An analgesia is disposed on a skin side. A needle guide is disposed on the needle side. The skin side is secure to an injection site so as to numb a person's skin prior to an injection. A needle is directed through the needle guide to the injection site. The securing mechanism may comprise compressing a suction cup to the injection site. In an embodiment, a needle path is disposed through a suction cup base and a breakable lid is disposed over the needle path so as to maintain a suction cup partial vacuum.

DESCRIPTION OF THE DRAWINGS

FIGS. 6A-C are front exploded perspective, back assembled perspective and mounted front perspective views, respectively, of an adhesive patch embodiment of an injection analgesia system.

DETAILED DESCRIPTION OF THE PREFERRED EMBODIMENT

Figure 1A:
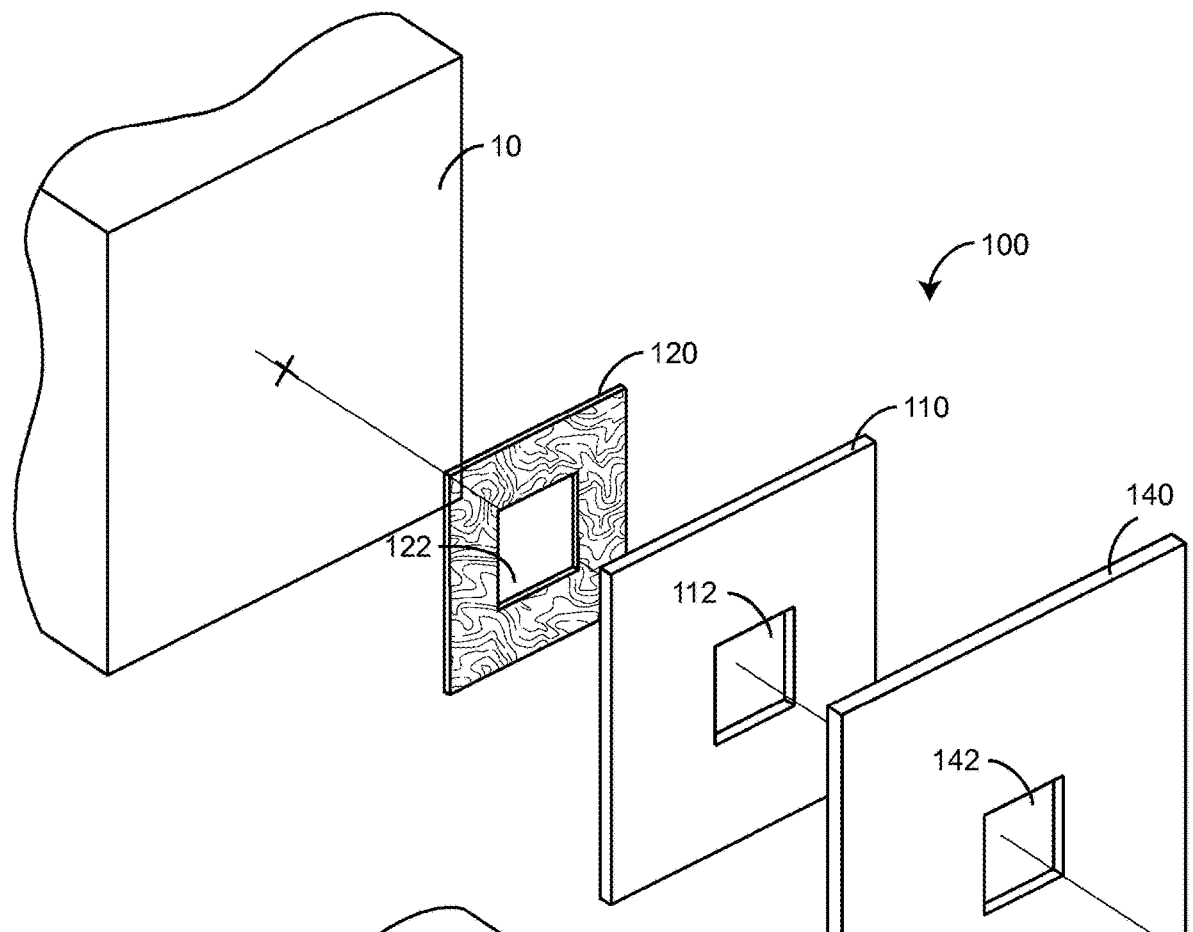
FIGS. 1A-B are exploded perspective and perspective views of a generalized injection analgesia system applied to a skin surface.
Figure 1B:
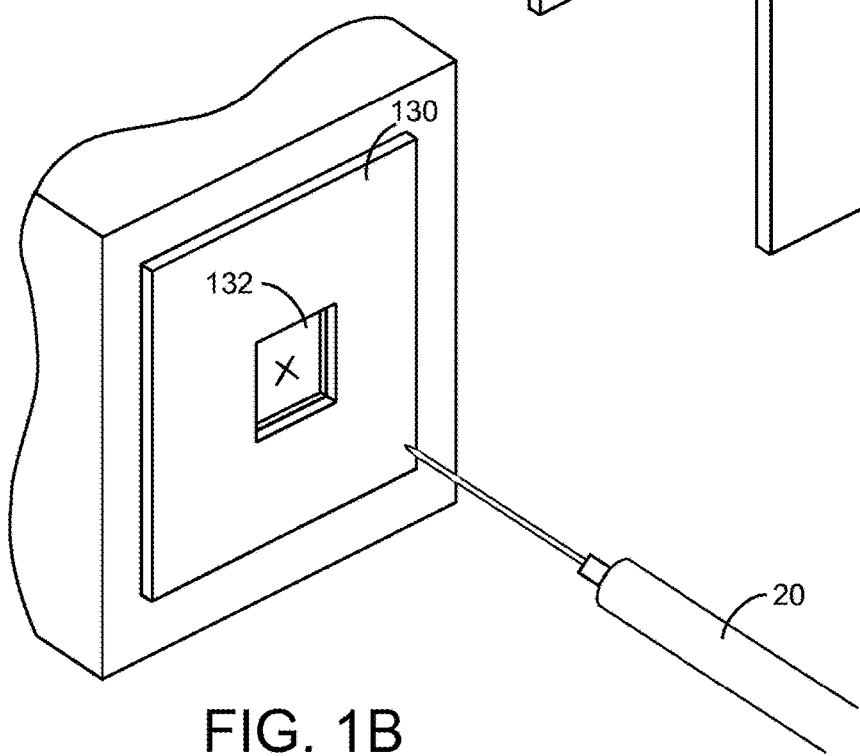

FIGS. 1A-B illustrate a generalized injection analgesia system 100 that advantageously numbs a patient's skin around an injection site. An injection window 132 advantageously guides a caregiver's injection placement to a relatively small area while allowing standard injection procedures to be followed, such as stretching the skin and puncturing the site with a jabbing motion. The injection analgesia system 100 has a needle shield 110 and an analgesia 120, which are layered together 130 and applied to a skin surface 10. A needle shield window 112 and a analgesia window 122 align to form the injection window 132. The needle shield 110 may be manufactured of various hygienic materials, such as medical-grade plastic, and a mild adhesive may be applied to the skin side of the shield 110 around the periphery of the analgesia 120 so as to removably adhere the shield 110 and analgesia 120 to the skin surface 10. Advantageously, the needle shield may fold and/or wrap around the injection needle for sharp object protection during and after needle disposal, as described with respect to FIGS. 2A-B, below.

As shown in FIGS. 1A-B, in an embodiment an attachment layer 140 having an attachment layer window 142 is disposed proximate needle shield 110 opposite the analgesia 120. The attachment layer 140 has adhesive disposed around the outer edges of the attachment layer 140, which extends beyond the edges of the needle shield 110. In this manner, the attachment layer 140 secures the needle shield 110 to the skin surface 10.

Figure 2A:
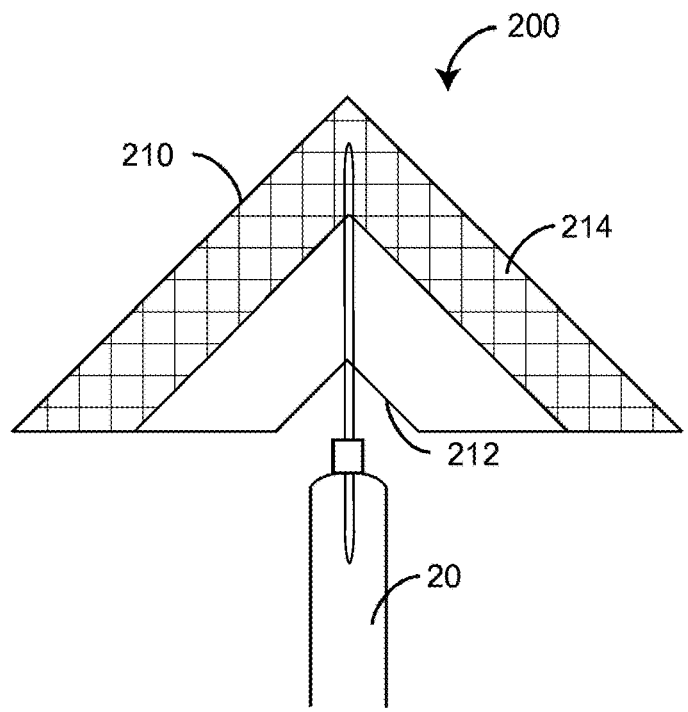
FIGS. 2A-B are folded and wrapped side-views, respectively, of an injection needle shield.
Figure 2B:
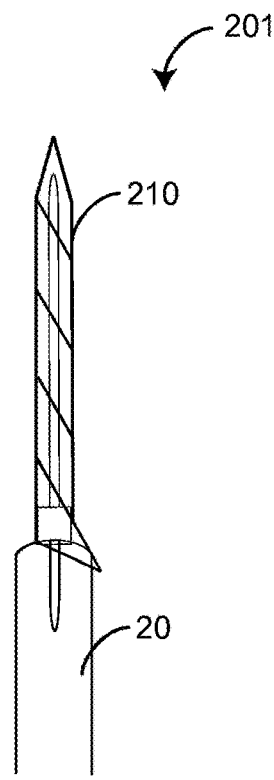

FIGS. 2A-B illustrate an injection needle shield 200 enclosing a used injection needle 20. FIGS. 2A-B are side-views of an injection analgesia system 200 after removal of a needle shield 210 from a skin surface and fully-enclosing the injection needle point by folding the needle shield 210 over the needle point (FIG. 2A) and, optionally, wrapping the shield 210 around the needle point (FIG. 2B). In an embodiment, the needle shield 200 has adhesive edges 214 allowing the folded shield 200 to adhere to itself so as to secure itself around the needle 20 as the needle extends through the shield window 212. In an embodiment, the needle shield 200 has interlocking extension disposed around the shield rim in lieu of or in addition to the adhesive 214, allowing portions of the needle shield to self-adhere and securely enclosing a substantial portion of the needle 20 and needle tip. In an embodiment, the needle shield 200 is in the form of a suction cup, such as described in detail with respect to FIGS. 3-5, below.

Figure 3A:
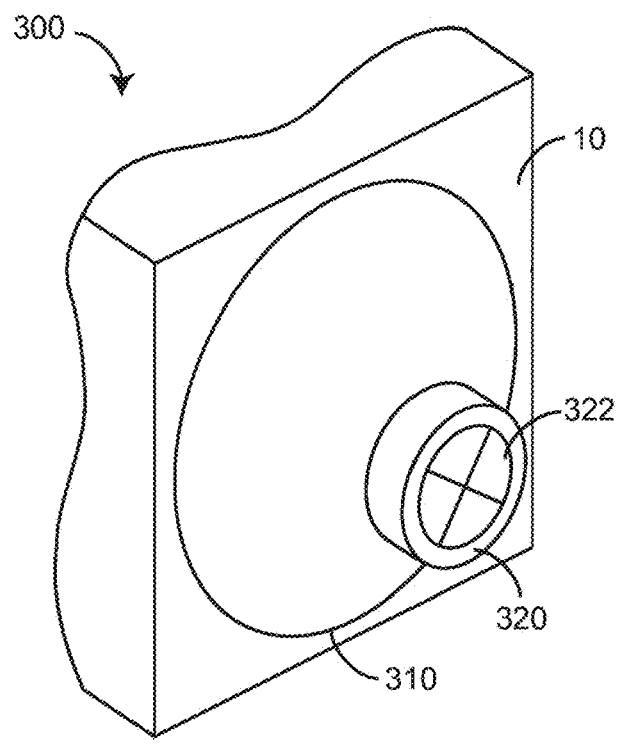
FIGS. 3A-B are mounted and injection perspective views, respectively, of a suction-cup embodiment of an injection analgesia system.
Figure 3B:
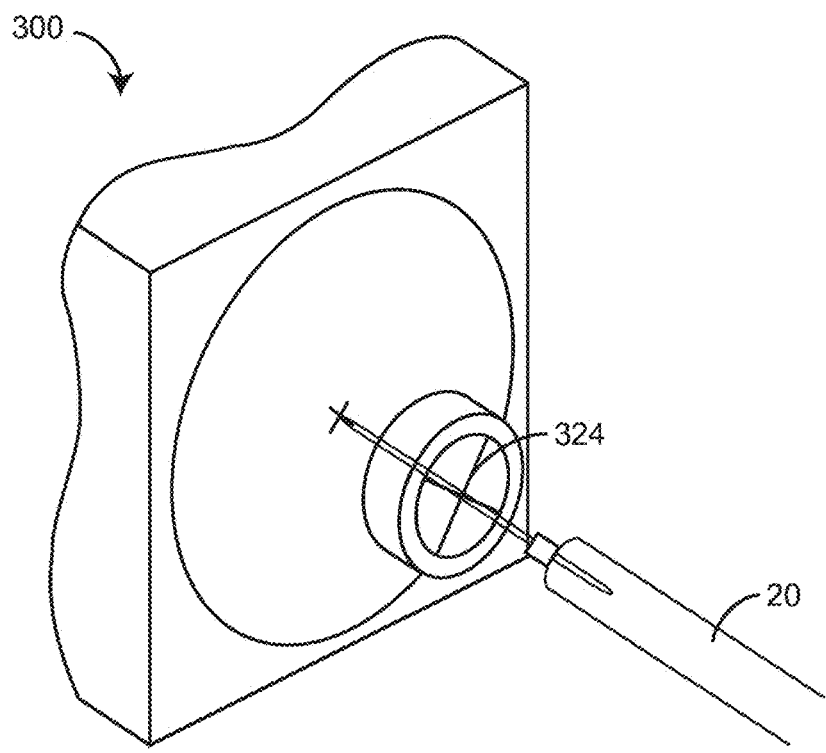

FIGS. 3A-B illustrate a suction-cup embodiment 300 of an injection analgesia system. The suction cup 300 has a flexible cup 310 and a rigid base 310 extending from the cup 310 center. The base 320 defines an opening 322 centrally disposed through the base 320 and extending into the cup 310. A scored lid 324 is disposed over the opening 322 so as maintain a partial vacuum when the suction cup 300 is pressed onto a skin surface 10. The scored lid 324 breaks when a needle 20 is jabbed, pressed or otherwise inserted into the opening 322 and into the skin so as to inject a serum or other medical fluid into a patient. Particular suction cup embodiments are described with respect to FIGS. 4-5, below.

FIGS. 4A-D illustrate an analgesia capsule suction-cup embodiment 400 of an injection analgesia system having a suction cup 410 needle shield. A capsule 420 is disposed within the suction cup 410 and an analgesia 430 is disposed within the capsule 420. As shown with respect to FIGS. 4A-B, the suction cup 410 has a generally conical shape with an open end 450 that tapers to a closed end 460. A generally cylindrical grip 470 is disposed on and extends from the closed end 460. A needle path 472 is centrally disposed through the cylindrical grip 470, and into the suction cup 410 proximate the analgesia capsule 430. As shown with respect to FIG. 4B, the closed end 460 is scored 462, holding a partial vacuum within the suction cup 410 until a needle pierces the closed end 460 during patient injection.

Figure 4A:
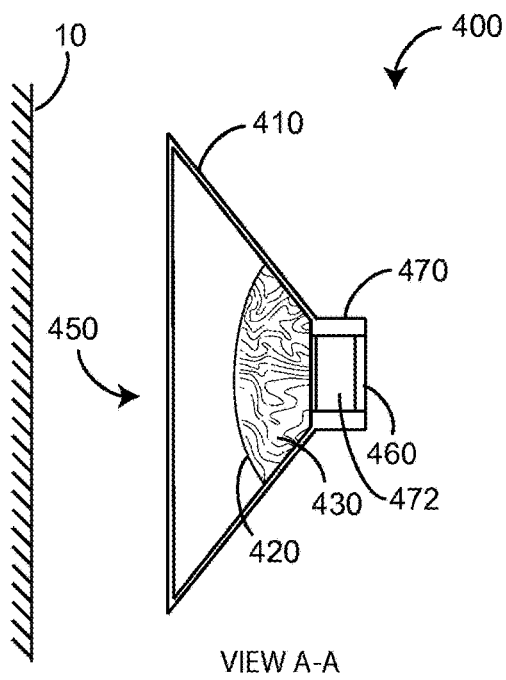
FIGS. 4A-D are un-mounted cross-sectional side and top views and mounted cross-sectional side and top views, respectively, of an analgesia capsule suction-cup embodiment of an injection analgesia system.
Figure 4B:
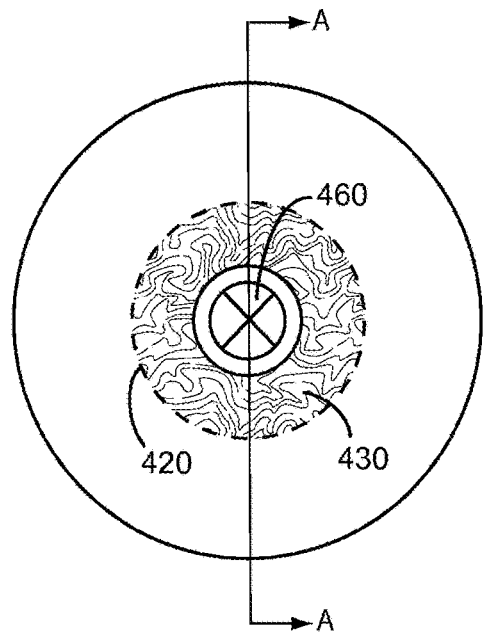
Figure 4C:
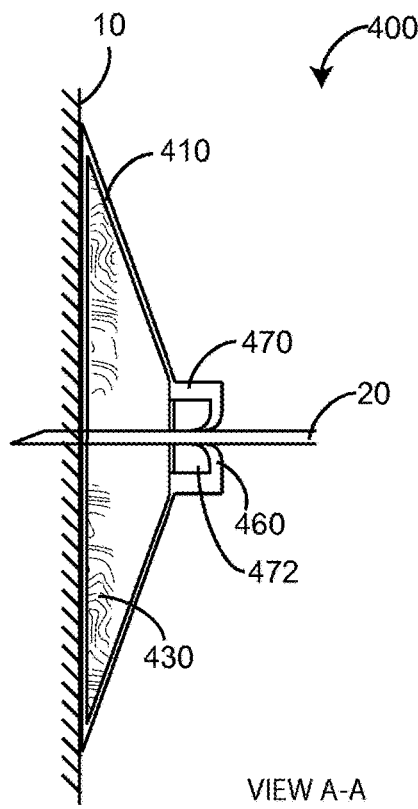
Figure 4D:
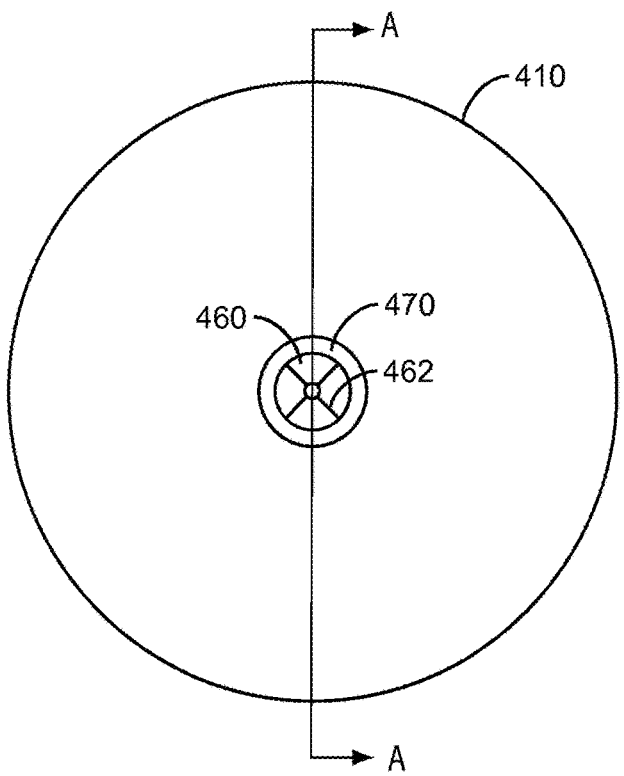

As shown with respect to FIGS. 4C-D, the suction cup 410 is applied to a skin surface 10 by grasping the grip 470 and pressing the suction cup 410 against the skin surface 10. In an embodiment, as the suction cup 410 expands against the skin surface 10, the capsule 420 bursts and the analgesia 430 is dispersed across the skin surface 10 and away from the cup 410 accordingly. After the analgesia has had time to take effect, the needle 20 is inserted through the scored lid 460 creating a needle opening 480. The needle 20 travels through the needle path 472 and into a patient's skin 10. In another embodiment, the capsule 420 is also disposed proximate the needle path 472 so that the needle 20 bursts the capsule 420 causing the analgesia 430 to disperse across the skin surface 10. In an embodiment, the needle path 172 serves as a guide to more accurately and steadily position the needle for injection.

Figure 5A:
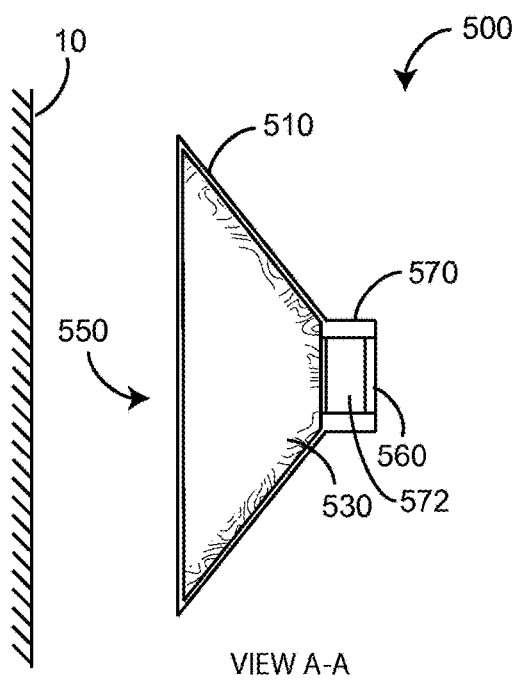
FIGS. 5A-D are un-mounted cross-sectional side and top views and mounted cross-sectional side and top views, respectively, of an analgesia film suction-cup embodiment of an injection analgesia system.
Figure 5B:
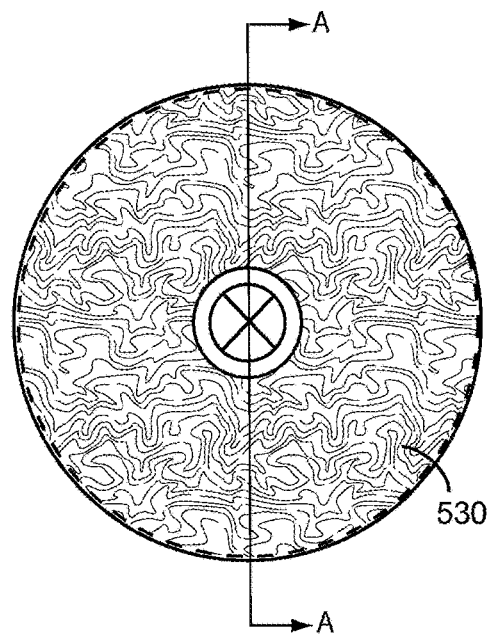
Figure 5C:
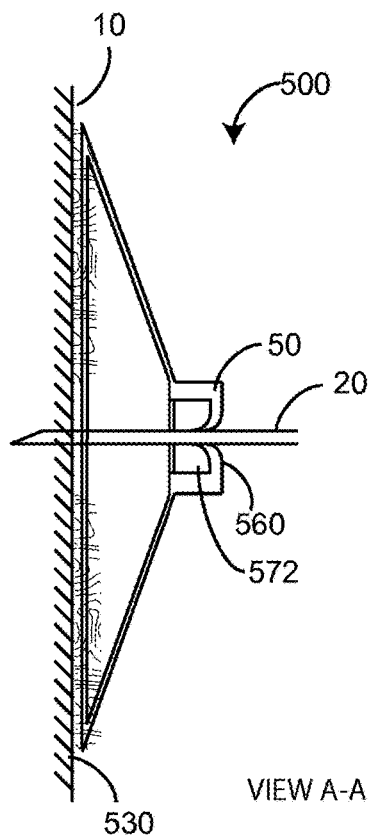
Figure 5D:
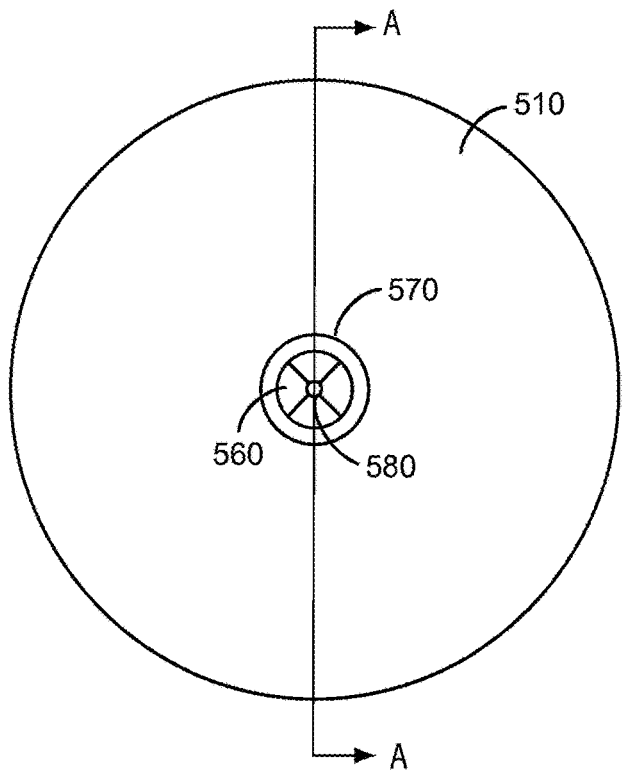

FIGS. 5A-D illustrate an analgesia film suction-cup embodiment 500 of an injection analgesia system. An analgesia 530 is pre-coated along the suction cup surface and contained by a tape or film (not shown) that removably adheres to the suction cup 510. The tape or film is removed prior to injection, and the analgesia is applied by over-extending the suction cup against the skin surface 10 and then releasing the suction cup to its normal applied position (FIG. 5C). After the analgesia 530 has had time to take effect, the needle 20 is inserted through the scored lid 560 creating a needle opening 580. The needle 20 travels through the needle path 572 and into a patient's skin 10.

FIGS. 6A-C illustrate an adhesive patch embodiment 600 of an injection analgesia system. As shown in FIG. 6A, an sealed adhesive patch 600 has an needle shield 610 defining a needle opening 612, an analgesia 620, an adhesive 630 and a removable backing 640. As shown in FIG. 6B, the backing 640 is removed so as to unseal an adhesive patch 601, exposing the analgesia 620 and adhesive 630 surfaces disposed on the needle shield 610. As shown in FIG. 6C, the exposed analgesia 620 and adhesive 630 surfaces of the adhesive patch 601 are pressed against a patient's skin 10 so as to adhere the adhesive patch 601 to the patient 10. After waiting a specified time period for the analgesia 620 to take affect, a painless injection is made through the patch window 650, the patch 601 removed and discarded.

An injection analgesia system has been disclosed in detail in connection with various embodiments. These embodiments are disclosed by way of examples only and are not to limit the scope of the claims that follow. One of ordinary skill in art will appreciate many variations and modifications.

What is claimed is:

1. A needle shield for shielding a used injection needle, the needle shield comprising:
    a shield portion having a first side and a second side, the shield portion having a predefined surface area; and
    a securing portion extending along a periphery of the shield portion on at least one of the first or second sides,
    wherein the shield portion is configured to wrap around a needle body of the used injection needle, the securing portion configured to couple to the shield portion such that the needle shield adheres to itself as the shield portion wraps around the needle body to securely enclose a portion of the used injection needle including a needle tip.

2. The needle shield of claim 1, wherein the securing potion comprises an adhesive.

3. The needle shield of claim 1, wherein the needle shield wraps spirally around the substantial portion of the used injection needle.

4. The needle shield of claim 1, wherein the needle shield comprises medical-grade plastic.

5. The needle shield of claim 1, wherein the needle shield is flexible.

6. A dual-use needle shield for providing analgesia to a patient during an injection procedure and shielding a used injection needle, the needle shield comprising:
    a shield portion having a first side and a second side, when in use, the first side configured to face away from the patient and the second side configured to face the patient, wherein the second side comprises an analgesia; and
    a securing portion extending along a periphery of the shield portion,
    wherein prior to or during the injection procedure, an injection needle is configured to extend through the shield portion from the first side to the second side, the analgesia configured to numb a skin surface enclosed within the second side of the shield portion, and
    wherein after the injection procedure, the shield portion is configured to wrap around a needle body of the used injection needle, the securing portion configured to couple to the shield portion such that the needle shield adheres to itself as the shield portion wraps around the needle body to securely enclose a portion of the used injection needle including a needle tip.

7. The needle shield of claim 6, wherein the securing potion comprises an adhesive.

8. The needle shield of claim 6, wherein the securing potion comprises interlocking extensions.

9. The needle shield of claim 6, wherein the securing potion comprises an adhesive and interlocking extensions.

10. The needle shield of claim 6, wherein the shield portion is flexible.

11. The needle shield of claim 6, wherein the needle entry window comprises a breakable scored lid.

12. A method of providing analgesia to a patient during an injection procedure and shielding a used injection needle using a dual-use needle shield, the method comprising:
- prior to an injection procedure, advancing an injection needle through the needle shield from a first side to a second side of the needle shield, the second side comprising an analgesia configured to numb a skin surface enclosed within the second side of the needle shield; and
- after the injection procedure, wrapping the needle shield around a needle body of the used injection needle,
- wherein the needle shield further comprises a securing portion around a periphery of the needle shield, the securing portion configured to adhere to the needle body and to the needle shield itself as the needle shield is wrapped around the needle body so as to securely enclose a portion of the used injection needle including a needle tip.

* * * * *